United States Patent [19]

Gluckman et al.

[11] Patent Number: 5,420,111
[45] Date of Patent: May 30, 1995

[54] IGF-1 AND RELATED COMPOUNDS IN PREGNANCY

[75] Inventors: Peter D. Gluckman; Geoffrey R. Ambler, both of Auckland; Bernhard H. Breier, Hamilton, all of New Zealand

[73] Assignee: Auckland Uniservices Limited, Auckland, New Zealand

[21] Appl. No.: 969,229
[22] PCT Filed: Jul. 10, 1991
[86] PCT No.: PCT/AU91/00309
§ 371 Date: Feb. 10, 1993
§ 102(e) Date: Feb. 10, 1993
[87] PCT Pub. No.: WO92/00754
PCT Pub. Date: Jan. 23, 1992

[30] Foreign Application Priority Data

Jul. 10, 1990 [NZ] New Zealand .................. 234439

[51] Int. Cl.$^6$ ..................... A61K 37/36; C07G 7/00
[52] U.S. Cl. ........................................ 514/12; 514/21
[58] Field of Search ........................... 514/12, 21

[56] References Cited

FOREIGN PATENT DOCUMENTS

| | | |
|---|---|---|
| 54306 | 10/1986 | Australia . |
| WO12018 | 8/1991 | Australia . |
| 0267015 | 5/1988 | European Pat. Off. . |
| 2488804 | 2/1982 | France . |
| 2085891 | 5/1992 | United Kingdom . |
| WO10348 | 7/1991 | . |

OTHER PUBLICATIONS

Biosis Abstract No. 87:84016; and J. Perinet. Med., vol. 14, No. 3, 1986; 163–169.
Pediatri Research, vol. 26, No. 6, 1988, pp. 663–667; J. W. Collins et al; "Human placental lactogen administration in the pregnant rat": acceleration of fetal growth.
Chemical Abstracts, vol. 101, No. 23, 1984; S. J. Pilistine et al: "Placental lactogen administration reverses the effect of low protein diet on maternal and fetal serum somatomedin levels in the pregnant rat" abst. No. 20435s.
Journal of Developmental Physiology, vol. 13, 1990, pp. 189–197; C. T. Jones et al; "Studies on the growth of the fetal guinea pig". The effects of nutritional manipulation on prenetal growth and plasma somatomedin activity and IGF factor concentrations.
Endocrimology, vol. 126, No. 4, 1990, pp. 2062–2067; M. L. Davenport et al.: "Effect of maternal fasting on fetal growth, serum insulin like growth factors, and tissue IGF messenger ribonucleic acid".
Chemical Abstracts, vol. 96, No. 17, 1982; D. J. Hill et al.: "Sometomedins and fetal growth", abst. No. 136725e.
C. T. Jones, H. N. Lafeber, T. P. Rolph, J. T. Parer, "Studies on the growth of the fetal guinea pig. The effects of nutritional manipulation on prenatal growth and plasma somatomedin activity and insulin-like growth factor concentrations", Jrnl of Development Physiology, 13, 189–197, 1990.
Effects of Insulin–Like Growth Factors I and II on Growth and "Differentiation of Transplanted Rat Embryos and Fetal Tissues", Endocrinology, vol. 124, No. 6, 3077–3082, 1989.

Primary Examiner—Howard E. Schain
Assistant Examiner—P. Lynn Touzeau
Attorney, Agent, or Firm—Browdy and Neimark

[57] ABSTRACT

Fetal growth is promoted and fetal growth retardation is reduced in mammals by increasing in a maternal host during pregnancy the active concentration of IGF-1 and /or IGF-2 and/or analogues thereof. The active concentration of IGF-1 and/or IGF-2 and/or analogues thereof may be increased either by directly administering to the maternal host IGF-1 and/or IGF-2 and/or analogs thereof or by administering another compound which, upon being so administered, causes an increase in the active concentration of IGF-1 and/or IGF-2 and/or analogues thereof in the maternal host.

9 Claims, 1 Drawing Sheet

IGF-1 AND RELATED COMPOUNDS IN PREGNANCY

TECHNICAL FIELD

This invention relates generally to a method and/or medicament for reducing fetal growth retardation and relates particularly though not necessarily solely to the use of maternally administered IGF-1, IGF-2 or analogues thereof or a combination of these compounds to promote fetal growth by reducing maternal constraint.

BACKGROUND ART

Fetal growth retardation is a major cause of perinatal morbidity and mortality both in farm animals and in man.

In man, intrauterine growth retardation is a major cause of perinatal death either due to late abortion, stillbirth or neonatal death particularly in prematurely delivered infants. No effective intrauterine therapy is known even though its diagnosis in utero by ultrasound for example is routine. The main therapy is bedrest. Growth retarded infants who survive have a far greater risk of asphyxial brain damage leading to sensory defects, cerebral palsy, learning disorders, epilepsy, or intellectual retardation. They also may exhibit severe and continuing growth failure.

In farm animals, intrauterine growth retardation leads to a greater risk of perinatal loss particularly from stillbirth or from hypothermia (due to insufficient metabolic fuel available after birth). Growth retardation often persists and is seen as the "runt" which causes a large economic loss to farmers. Such runts are common in sheep, cattle, goats, deer, and particularly in pigs. No effective therapy or prophylactic approach other than selective breeding is known. The "runt problem" has limited the ability for new breeds of high fecundity (e.g. the Boroola merino sheep) to be economically introduced.

In one publication (Blair et al., *Endo* 123: 1690–1692, 1988) experiments where described wherein three lines of mice where derived by genetic selection based on their levels of IGF-1 secretion. These were termed "control" mice and "high line" and "low line" IGF-1 mice. It was found that mice secreting higher amounts of IGF-1 had larger placentae and fetuses than the conrol and low-line mice.

However, the above study did not define whether the observation that larger fetuses were born to high-line IGF-1 mice was a coincidence based on the experimental design, or whether it was due to a difference in fetal, placetal or maternal IGF-1 secretion.

Contemporary publications indicate that IGF-1 does not cross the placenta (Davenport et al., i Endo. 127: 1278–1287, 1990). Thus, it appeared unlikely that the increase in fetal size was due to an increase in maternal IGF-1 secretion. In light of this, there has been no interest in the potential for maternally administered IGF-1 to affect fetal development.

Accordingly, it is an object of the invention to provide a method and/or medicament for reducing fetal growth retardation which will at least provide the public with a useful choice.

It is a further object of the invention to provide a method and/or medicament for promoting fetal growth which will at least provide the public with a useful choice.

DISCLOSURE OF INVENTION

In a first aspect the invention relates to a method of reducing fetal growth retardation and/or promoting fetal growth in mammals comprising the step of increasing the active concentration(s) of IGF-1 and/or IGF-2 and/or analogues of said IGF-1 or IGF-2 within the maternal host during pregnancy.

The invention also consists in a medicament suitable for reducing fetal growth retardation and/or promoting fetal growth in meals comprising IGF-1, IGF-2 or analogues of said IGF-1 or IGF-2 or a mixture of two or more of these optionally provided in a pharmaceutically acceptable carrier or diluent.

The invention also relates to a medicament suitable for reducing fetal growth retardation and/or promoting fetal growth in mammals comprising a compound which, on administration to a pregnant female, increases the active concentration of IGF-1 and/or IGF-2 and/or naturally occuring analogues of said IGF-1 or IGF-2 optionally provided in a pharmaceutically acceptable carrier or diluent.

Further, the invention may be said to consist in the use of IGF-1, IGF-2 or analogues of said IGF-1 or IGF-2 or a mixture of two or more of these in the preparation of a medicament for reducing fetal growth retardation and/or promoting fetal growth in mammals.

Also, the invention relates to the use of a compound which, on administration to a pregnant female, increases the active concentration of IGF-1 and/or IGF-2 and/or naturally occuring analogues of said IGF-1 or IGF-2 in the preparation of a medicament for reducing fetal growth retardation and/or promoting fetal growth in mammals.

Although the present invention is defined broadly above, it will be appreciated by those skilled in the art that it is not limited thereto but that it includes embodiments of which the following description provides examples. Moreover, a better understanding of the invention will be gained from reference to the appended examples and figures.

BEST MODE FOR CARRYING OUT THE INVENTION

Figure 1:
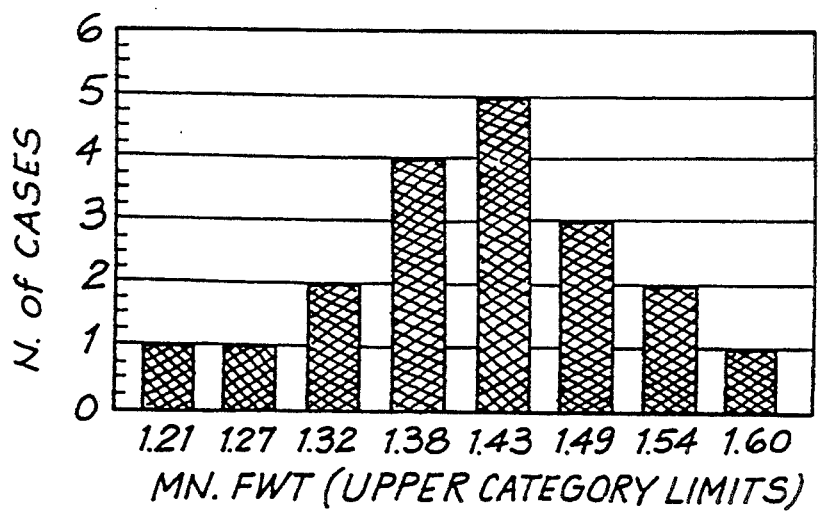
FIG. 1 shows the distribution of mean fetal weights for the saline treated controls in Example 3.
Figure 2:
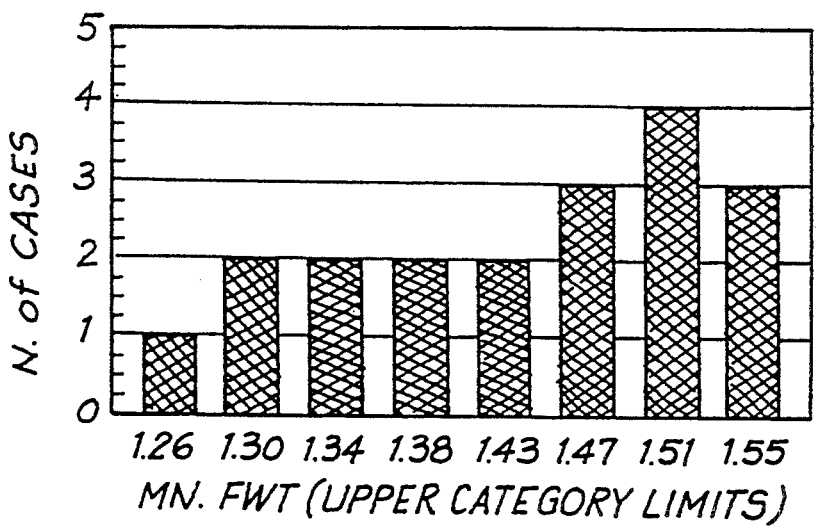
FIG. 2 shows the distribution of mean fetal weights for the IGF-1 treated rats in Example 3.
Figure 3:
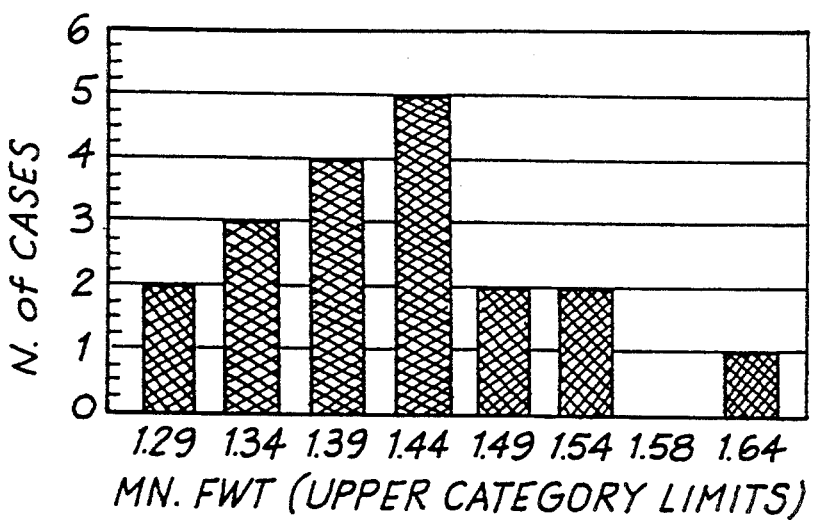
FIG. 3 shows the distribution of mean fetal weights for the bGH treated rats in Example 3.

This invention is based on the unexpected finding that fetal growth retardation resulting from maternal constraint can be significantly reduced by elevating the concentration of IGF-1 in the maternal host. This is totally unexpected over the prior art, particularly as it is known that IGF-1 does not cross the placenta. The results of the foregoing experiments show that administration of IGF-1 appears to have an indirect effect on fetal growth which is in the maternal compartment.

The invention relates to manipulating fetal growth in mammals. As a first aspect of this manipulation, the invention has application to fetal growth retardation and a method of reducing this phenomenon. By "reduce" is meant a decrease in the degree of fetal growth retardation and includes a complete inhibition of the signs of fetal growth retardation.

Fetal growth retardation may result as a consequence of "maternal constraint". Maternal constraint is the phenomenon by which uterine function and the maternal environment constrain fetal growth. It is generally reflected in a reduction in mean fetal size as the litter size increases. In normal mice, such maternal constraint explains over 50% of the variation in fetal size and similar extrapolations have been made to human pregnancy from birth weight analysis. For example, it explains the lower birth weight of twins. In domestic farm animals, this is seen in the lower birth size and increased mortality of polytocous breeds.

Without wishing to be bound by any theory, the applicants hypothesise that IGF-1 may mediate its action by interfering with the normal process of maternal constraint.

As a further and related application, the invention also provides a method of promoting fetal growth. By "promote" is meant an increase in the resultant fetal size of a pregnancy. The phrases "reducing fetal growth retardation" and "promoting fetal growth" are not mutually exclusive. In other words, by reducing fetal growth retardation an increase in fetal growth will generally result.

In both of the methods above, the critical step is that of increasing the active concentrations of IGF-1 and/or IGF-2 and/or analogues of these compounds within the maternal host during pregnancy. Most conveniently, this can be achieved by direct administration of these compounds. Alternatively, compounds which on administration to pregnant females, result in an elevation in the active concentration of IGF-1, IGF-2 or naturally occuring analogues thereof can be administered. By "active concentration" is meant the maternal concentration of the IGF-1 related compounds which are biologically active.

It will of course be appreciated that by IGF-1 and IGF-2 is meant Insulin-Like Growth Factors 1 and 2. These terms include naturally occurring human or animal IGF-1 and IGF-2 isolated and purified by known techniques as well as recombinant IGF-1 and IGF-2. IGF-1 and IGF-2 are manufactured using recombinant DNA techniques by several companies including GENENTECH INC., USA; KABI PHARMACIA, SWEDEN and PITMAN MOORE INC., USA.

Although the studies to be discussed herein concentrate on the use of IGF-1, the claims extend to IGF-2 and analogues of IGF-1 and IGF-2 as these are known to exert a similar biological effect to IGF-1 (Schoenle et al., Acta Endoc. 108: 167–174, 1985).

By "analogues" of IGF-1 and IGF-2 is meant compounds having the same therapeutic effect as IGF-1 or IGF-2 in humans and animals. These can be naturally occuring analogues of IGF-1 or IGF-2 (eg truncated IGF-1 or DES 1–3 IGF-1 synthesised by GENENTECH, INC. and KABI PHARMACIA) or any of the known synthetic analogues of IGF-1 and IGF-2.

The compositions are administered to pregnant females. As was shown in the foregoing examples, the composition can be administered at any time from conception onwards Desirably however, the medicament is administered at a time close to the time of birth of the fetus. The compositions can be administered by many different methods including subcutaneous, intramuscular or intravenous administration. However, the composition is desirably administered systemically into the blood stream of the pregnant female.

The applicants envisage that a suitable dosage range may for example be between 0.1 to 2000 micrograms of the composition per kilogram of body weight of the mammal per day. By composition is meant IGF-1, IGF-2 or their analogues or compounds which elevate the concentration of these compounds in mammals or a suitable mixture thereof.

The compositions could be administered prophylactically (eg. to animals to prevent "runting") or as a treatment wherein growth retardation of a fetus is apparent.

Routine techniques such as ultrasound could be carried out to establish whether or not a fetus is suffering fetal growth retardation for example. If fetal growth retardation is apparent, the compositions could be administered to the mother of such a pregnancy by the techniques described above.

The invention also relates to the manufacture of a medicament for reducing fetal growth retardation and/or promoting fetal growth. The medicament comprises IGF-1, IGF-2 or analoguss thereof. Also, the medicament can comprise compounds which elevate the active concentrations of IGF-1 or IGF-2 or naturally occuring analoguss thereof upon administration to a pregnant female.

The medicament can be manufactured using the following techniques. The compounds IGF-1 and IGF-2 and some of their respective analogues can for example be obtained commercially from GENENTECH INC., KABI PHARMACIA and PITMAN MOORE INC. These compounds may be isolated from natural sources or prepared via recombinant DNA techniques. The DNA sequences corresponding to IGF-1 and IGF-2 and some of their analogues are known. Accordingly, the recombinant DNA techniques outlined in New Zealand Patent Specification No. 208339 could be used to prepare the compounds.

Similarly, the compounds which elevate the concentration of IGF-1, IGF-2 or naturally occuring analogues thereof can be isolated from natural sources or prepared by recombinant DNA techniques.

The compounds can be provided alone or a combination of two or more of these compounds could be used. The IGF-1 and related compounds are desirably provided in a pharmaceutically acceptable carrier or diluent. Pharmaceutical carriers or diluents such as those presently known in the art could be used. Thus, a medicament can be prepared which can be used to reduce or eliminate fetal growth retardation in mammals and thus promote fetal growth.

The invention also relates to the use of IGF-1, IGF-2 or analogues of said IGF-1 and IGF-2 or compounds which elevate the level of these compounds in humans in the preparation of a medicament suitable for reducing fetal growth retardation as well as promoting fetal growth.

In the following studies supporting the invention we have found the following:
1. Administration of recombinant IGF-1 to pregnant female mice reduces or abolishes maternal constraint.
2. IGF-1 clearly reduces maternal constraint when compared to saline treated control rats and rats treated with another growth factor, bovine growth hormone.

EXAMPLE 1

The objective of this study was to establish the effects of administering recombinant IGF-1 to pregnant female mice.

Swiss female mice identified by tail markings were mated with males of the same strain. Successful matings were observed the next morning by the presence of a vaginal plug. The females were then treated throughout pregnancy with either 100 µl physiological saline containing 0.1 mol/liter acetic acid given subcutaneously every eight hours (the control mice) or with recombinant human IGF-1. These mice were administered with 10 µg/injection of IGF-1 dissolved in 100 µl of saline containing 0.1 mol/liter acetic acid. The IGF-1 was obtained from GENENTECH INC., USA.

The animals were housed under standard lighting conditions and fed mice chow and libitum. On day 18, they were sacrificed by decapitation and the number and total weight of the fetuses measured. All weighings were carried out using an electronic balance accurate to <0.1 gm. Covariant analysis was used to exclude any effects related to IGF-1 affecting maternal size.

The major index recorded was that of the relationship between mean fetal weight and litter size using linear regression techniques. In normal animals there is a negative relationship between mean fetal weight and litter size. This reflects the limited capacity of the maternal-uterine-placental unit to transfer sufficient nutrients to maintain optimal growth of all fetuses. This phenomenon is termed "maternal constraint" and comparable mechanisms are operative in human pregnancy (Gluckman et al., *Acta Paediatrica Scandinavica Supplement* 367:105–110, 1990).

There was no effect of treatment on placental weight or litter size.

| Treatment | RESULTS Correlation Coefficient Mean Fetal Weight Versus Litter Size | No. Mice Tested |
| --- | --- | --- |
| 100 µl saline with 0.1 mol/liter acetic acid | r = −0.869 p < 0.01 | 9 |
| 100 µl saline with 0.1 mol/liter acetic acid and 10 µg recombinant IGF-1 | r = 0.178 p = not significant | 10 |

Thus, administration of IGF-1 to pregnant female mice appears to result in a reduction in the negative correlation between mean fetal weight and litter size.

EXAMPLE 2

The objective of this study was to establish the effects of administering IGF-1 to control mice and mice secreting low levels of IGF-1.

Control mice and low line mice described on page 9 were tested. The mice were treated when 100 days old. In the control lines, nine dams were treated with saline and nine with IGF-1 (see EXAMPLE 1 for the nature of these treatments). In the low line eight dams were treated with saline and eight with IGF-1. Linear regression was then performed as described for Example 1.

| Treatment | Mice Type | Correlation Coefficient mean fetal weight versus litter size | No. mice Tested |
| --- | --- | --- | --- |
| 100 µl saline with 0.1 mol/liter acetic acid | Control | r = −0.76 p < 0.02 | 9 |
| 100 µl saline with 0.1 mol/liter acetic acid and 10 µg recombinant IGF-1 | Control | r = −0.114 p = Not significant | 9 |
| 100 µl saline with 0.1 mol/liter acetic acid | Low Line | r = −0.412 p = 0.2 | 8 |
| 100 µl saline with 0.1 mol/liter acetic acid and 10 µg recombinant IGF-1 | Low Line | r = −0.067 p = Not significant | 8 |

In conclusion, the control mice showed similar results to the mice tested in Example 1. That is, administration of IGF-1 resulted in a reduction of the negative correlation between litter size and mean fetal weight.

In the low line mice, although the small number of animals studied reduced the significance in the saline treated controls, nevertheless IGF-1 treatment abolished the trend towards a negative correlation.

EXAMPLE 3

The objective of this study was to compare the effects of administering IGF-I and another growth factor, bGH Wistar bred (100) female rats of approximately 270 gm and about 90–100 days of age were weighed. Those of poor condition or extremely low body weight were excluded. The animals were identified by tail markings placed prior to mating. In groups of 20 the females were placed with male rats of the same breed overnight. The next morning mating was checked for by the presence of a vaginal plug. The successfully mated animals were weighed and divided into three treatment groups. Those not mated were re-mated the following night with additional fresh females. The mating programme was repeated until 80 females had mated.

On the morning after mating under a brief period (<2 min) of inhaled halothane anaesthesia a microosmotic pump (Alzet Corporation, USA, model 2ML4) was inserted subcutaneously on the back of the animals. The pump contained either one of three solutions:

(a) Placebo: 2 ml of 0.1 mol/liter acetic acid
(b) IGF-1: 2 ml of recombinant human IGF-1 composition (supplied by GENENTECH INC., San Francisco). This was calculated to deliver 1 µg/gm body weight/day of IGF-1 by dissolving 10 mg of IGF-1 in 2.2 ml of 0.1 mol/liter acetic acid and loading 2 ml into the Alezet osmotic pump.
(c) bGH: Recombinant bovine growth hormone donated by American Cyanamid. The bGH was also loaded into Alzet pumps. The dose delivered was 0.66 µg/day achieved by dissolving 7 mg bGH in 200 µl of 0.1 mol/liter sodium bicarbonate, then adding 2 ml of saline and the osmotic pump was loaded to 2 ml.

All three solutions were sterilised prior to loading by syringe into the pumps by passage through an Acrodisc filter.

The animals were housed under standard lighting conditions and fed rat chow ad libitum.

On day 19 after mating, the animals were again anaethetised, weighed, and a blood sample was obtained by cardiac puncture. The rat was then dissected to obtain carcass weight, fetal and placental number, individual fetal and placental weights.

19 litters for each treatment were obtained.

The principal mode of analysis was again to examine the relationship between fetal weight and litter size.

Data was analysed using the Stats+ statistical software package.

The following relationships were obtained

| | Treatment | No. Litters Tested | Correlation Coefficient mean fetal weight versus litter size | |
|---|---|---|---|---|
| A. | Saline | 19 | $r = 0.43$ | $p < 0.06$ |
| B. | IGF-1 | 19 | $r = +0.36$ | $p < 0.1$ |
| C. | bGH | 19 | $r = -0.37$ | $p < 0.1$ |

By the technique of the combined test for heterogeneity of slopes it can be shown that whereas there is no difference between the bGH and saline treated mice in the relationship between fetal size and litter size, with IGF-1 therapy there is a significant change in the relationship such that fetal size is no longer inversely correlated with litter size.

In contrast, the anticipated relationship between placental size and litter size is maintained.

| | Treatment | No. mice Tested | Correlation Coefficient mean placental weight versus litter size | |
|---|---|---|---|---|
| A. | Saline | 19 | $r = -0.52$ | $p < 0.05$ |
| B. | IGF-I | 19 | $r = -0.52$ | $p < 0.05$ |
| C. | bGH | 19 | $r = -0.64$ | $p < 0.01$ |

As a consequence whereas in normal pregnancy there is a positive correlation between placental and fetal weight this was lost after IGF-1 therapy.

| | Treatment | No. mice Tested | Correlation Coefficient mean placental size versus fetal weight | |
|---|---|---|---|---|
| A. | Saline | 19 | $r = 0.47$ | $p < 0.05$ |
| B. | IGF-I | 19 | $r = 0.49$ | $p < 0.05$ |
| C. | bGH | 19 | $r = 0.37$ | $p = < 0.01$ |

Again by the combined test for heterogeneity of slopes the IGF-1 treated group differed from the other two.

Further evidence for the effect of IGF-1 on fetal development is seen in the analysis of the distribution of fetal weights.

In the histograms the ordinate MN.FWT (upper category limits) refers to the way the statistics package divides the data into eight bins. The mean fetal weights are grouped. The number under each bar refers to the upper limit for the fetal weight in that bar. For example, for the saline data the bars are <1.21, between 1.22 and 1.27 and so on.

As shown in the attached graphs whereas the mean fetal weights distributed normally for the saline and bGH treated groups this was not the case for the IGF-1 treated group.

By univariate analysis there was significant skewing of the fetal weights only in the IGF-1 treated group.

These observations suggest that maternal IGF-1 alters placental function such that it is no longer limiting on fetal growth. Thus IGF-1 appears to reduce maternal constraint. The results also show that administration of IGF-1 to a pregnant female does not appear to increase placental size and this finding is contrary to the art. Accordingly, the effect of IGF-1 is clearly in the maternal compartment as IGF-1 does not cross the rat placenta (see Davenport et al, Endo 127 :1278–1286, 1990).

INDUSTRIAL APPLICABILITY

In conclusion, the foregoing experiments show that IGF-1 clearly results in a reduction in the negative correlation between mean fetal weight verses litter size. Accordingly, IGF-1 and related compounds would appear to have a useful application in reducing fetal growth retardation and promoting fetal growth. In the past, the only known intrauterine therapy for humans is bed rest. In animals, selective breeding is the only preventative measure available to reduce the number of growth retarded infants born in a population. The foregoing invention provides a novel medicament which can be used to treat fetal growth retardation in humans and animals.

The following, non-limiting applications of the invention are envisaged:

(i) Human medicine. In man, this invention is likely to be used by systemically treating mothers diagnosed as having growth retarded fetuses with IGF-1 or related compounds to improve fetal outcome. It also may be a useful prophylactic approach to reduce the likelihood of growth retardation where multiple pregnancy is diagnosed early, or where it is induced by in-vitro fertilisation or other new birth technologies or where there is a strong past history in the woman of perinatal loss due to growth retardation or where there growth retardation has been recurrent.

(ii) Farming. It is likely that this invention will lead to the use of IGF-1 or related compounds to prophylactically treat farm animals with a high risk of perinatal loss or persistent runting. The most important applications will be in the pig industry but applications to sheep, to deer, dairy and beef cattle and other domestic species are also envisaged.

(iii) Veterinary practice. Cats and dogs are polytocous species and for valuable pedigree stock prophylactic IGF-1 or related compound therapy is likely to improve outcome particularly as runt animals have little value.

We claim:

1. A method of reducing fetal growth retardation in a maternal mammalian host during pregnancy or of promoting fetal growth in a maternal mammalian host during pregnancy, comprising the step of administering to a maternal mammalian host during pregnancy a compound or composition which causes the active concentration of at least one of IGF-1 or DES 1–3 IGF-1, to be increased within the maternal host.

2. A method as claimed in claim 1, comprising the step of administering to the maternal mammalian host an amount sufficient to reduce fetal growth retardation, of at least one compound selected from the group consisting of IGF-1 and DES 1-3 IGF-1, optionally provided in a pharmaceutically acceptable carrier or diluent.

3. A method as claimed in claim 2, wherein the dosage range administered is from about 0.1 to 2000 μg of said at least one compound per kilogram of body weight of said maternal host per day.

4. A method as claimed in claim 1 wherein the dosage range administered is from about 0.1 to 2000 μg of said compound per kilogram of body weight of said maternal host per day.

5. A method as claimed in claim 4 wherein said administration is subcutaneous, intramuscular or intravenous.

6. A method as claimed in claim 1 including the preliminary step of diagnosing growth retardation of a fetus of said maternal host.

7. A method as claimed in claim 6 wherein said diagnosing step is by an ultrasound technique.

8. A method in accordance with claim 2 wherein said compound is IGF-1.

9. A method in accordance with claim 2, wherein said compound is IGF-1 DES 1-3.

* * * * *